US008784319B2

(12) United States Patent
Ishidai et al.

(10) Patent No.: US 8,784,319 B2
(45) Date of Patent: Jul. 22, 2014

(54) ULTRASONIC PROBE AND ULTRASONIC DIAGNOSTIC DEVICE

(75) Inventors: Hiroshi Ishidai, Hachioji (JP); Hiromi Akahori, Hino (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 189 days.

(21) Appl. No.: 13/146,464

(22) PCT Filed: Feb. 5, 2010

(86) PCT No.: PCT/JP2010/051687
§ 371 (c)(1),
(2), (4) Date: Jul. 27, 2011

(87) PCT Pub. No.: WO2010/092907
PCT Pub. Date: Aug. 19, 2010

(65) Prior Publication Data
US 2012/0022378 A1    Jan. 26, 2012

(30) Foreign Application Priority Data

Feb. 12, 2009 (JP) ................................. 2009-029574

(51) Int. Cl.
*A61B 8/00* (2006.01)
*A61B 8/14* (2006.01)

(52) U.S. Cl.
USPC ........... 600/459; 600/437; 600/443; 310/334; 310/336

(58) Field of Classification Search
USPC ................... 600/459, 443, 437; 310/334, 336
See application file for complete search history.

(56) References Cited

U.S. PATENT DOCUMENTS

| 4,651,310 A | * | 3/1987 | Kaneko et al. ................. 367/140 |
| 5,651,365 A | * | 7/1997 | Hanafy et al. ................. 600/459 |
| 2007/0216257 A1 | | 9/2007 | Fujimura et al. |
| 2008/0021328 A1 | | 1/2008 | Habu et al. |

FOREIGN PATENT DOCUMENTS

| JP | 61-293098 A | 12/1986 |
| JP | 2-99041 A | 4/1990 |
| JP | 7-123497 A | 5/1995 |
| JP | 8-307995 A | 11/1996 |
| JP | 9-215095 A | 8/1997 |

(Continued)

OTHER PUBLICATIONS

International Search Report dated Mar. 23, 2010 issued in International Appln. No. PCT/JP2010/051687.

(Continued)

*Primary Examiner* — Long V. Le
*Assistant Examiner* — Farshad Negarestan
(74) *Attorney, Agent, or Firm* — Holtz Holtz Goodman & Chick PC

(57) ABSTRACT

An ultrasonic probe includes at least one transmission element layer for transmitting ultrasonic waves, at least one reception element layer for receiving ultrasonic waves and which is provided with an electrode on each of both surfaces opposed in a direction of a thickness thereof, and at least one matching layer for matching acoustic impedance. These layers are arranged in this order in a direction of transmitting the ultrasonic waves. The reception element layer is provided with a projecting portion projecting in a direction of elevation from upper and lower layers which sandwich the two electrodes respectively formed on both surfaces of the reception element layer, and at least one of the electrodes is formed by extending to the projecting portion.

5 Claims, 4 Drawing Sheets

(56) References Cited

FOREIGN PATENT DOCUMENTS

| JP | 10-84243 A | 3/1998 |
| JP | 10-112899 A | 4/1998 |
| JP | 2006-35003 A | 2/2006 |
| JP | 2006-320512 A | 11/2006 |
| JP | 2007-13944 A | 1/2007 |
| WO | WO2008/010509 A1 | 1/2008 |

OTHER PUBLICATIONS

Japanese Office Action dated Jun. 11, 2013 (and English translation thereof) in counterpart Japanese Application No. 2010-550496.

* cited by examiner

ULTRASONIC PROBE AND ULTRASONIC DIAGNOSTIC DEVICE

This application is a U.S. National Phase Application under 35 USC 371 of International Application PCT/JP2010/051687 filed on Feb. 5, 2010.

FIELD OF THE INVENTION

The present invention relates to an ultrasonic probe and ultrasonic diagnostic device.

DESCRIPTION OF RELATED ART

The ultrasonic diagnostic device is an image device for medical treatment capable of minimal invasion of the tomographic image of in-vivo soft tissue from the body surface by the ultrasonic pulse reflection method. Compared with other image devices for medical treatment, this ultrasonic diagnostic device is characterized by reduced costs and an enhanced level of safety without possible exposure to X-rays and other radiation, and is capable of blood flow imaging by means of the Doppler effect. This device has been used over an extensive range covering the circulatory system (coronary artery), digestive system (stomach and intestines), internal system (liver, pancreas and spleen), urinary system (kidney and bladder) and obstetric/gynecologic system.

Since the ultrasonic probe used in the aforementioned ultrasonic diagnostic device for medical treatment is required to provide transmission/reception of ultrasonic waves of a high level of sensitivity and resolution, the probe commonly uses an inorganic piezoelectric element known under the name of PZT. In this case, a single type probe consisting of a single probe or an array type probe consisting of a two-dimensional array of a plurality of probes is often used in the oscillation mode of the piezoelectric element for transmission. The array type probe provides a high-definition image and is widely used to provide a medical image for diagnostic examination.

In the meantime, the harmonic imaging diagnosis based on the harmonic signal provides a sharp diagnostic image that cannot possibly be obtained from the conventional B-mode diagnosis, and is coming to be established as a standard diagnostic method.

Harmonic imaging provides a great number of the following advantages, as compared to imaging by fundamental waves:

1. The reduced side lobe level ensures excellent signal-to-noise ratio, hence superb contrast resolution.
2. The beam width is reduced by higher frequency, with the result that resolution in the horizontal direction is improved.
3. The sound level is smaller at a short distance, and fluctuations in sound level are smaller so that multiplex reflection does not occur.
4. The attenuation beyond the focal point is on the same level as the fundamental waves, and a high level of deep velocity can be ensured, as compared with the ultrasonic wave wherein the harmonic frequency is used as the fundamental wave.

And so on.

In a proposed structure of the array type ultrasonic probe used in harmonic imaging, the piezoelectric oscillator for transmission is separated from the piezoelectric oscillator for reception so that the operation for transmission of ultrasonic waves is different from that for reception.

The piezoelectric oscillator for reception used in such an array type ultrasonic probe is preferably capable of receiving harmonic signals at a high sensitivity. However, since the transmission frequency of the inorganic piezoelectric element depends on the thickness of the inorganic piezoelectric element, the inorganic piezoelectric element must be processed in a more compact configuration as the received frequency is higher. This has resulted in manufacturing difficulties.

To solve the aforementioned problems, the present inventors have proposed a method for producing a highly sensitive ultrasonic probe, wherein an transmission piezoelectric element of a single layer or a laminated structure and a reception sheet-like piezoelectric ceramics are formed in a single layer or in a laminated structure in such a way that different piezoelectric elements are used separately for transmission and reception, and a highly sensitive organic piezoelectric material is employed for reception. (Patent Literatures 1, 2 and 3)

In the meantime, it is important to find out a proper method for connection between the electrode of the piezoelectric element used in the ultrasonic probe and the wiring material. Depending on the method of connection, the quality of the signal sent from the ultrasonic probe may be deteriorated or the performance and reliability of the ultrasonic diagnostic device may be affected.

In one of the methods proposed to meet this requirement, a side-mounted electrode is formed on the piezoelectric element, and is soldered with a lead wire (Patent Literatures 4 and 5). In another proposed method, a flexible printed substrate for signal is soldered with the electrode of the piezoelectric element (Patent Literature 6).

In a further method having been proposed, to downsize the ultrasonic probe, an electrode outlet port extending from the laminated portion of the piezoelectric element is formed on electrodes laminated on both surfaces of the piezoelectric element (Patent Literature 7).

EARLIER TECHNOLOGICAL LITERATURE

Patent Literature

Patent Literature 1: Unexamined Japanese Patent Application Publication No. 2008-188415
Patent Literature 2: Official Gazette of International Publication No. 2007/145073
Patent Literature 3: Official Gazette of International Publication No. 2008/010509
Patent Literature 4: Japanese Patent Application Publication No. 3313171
Patent Literature 5: Unexamined Japanese Patent Application Publication No. Hei. 7 (1995)-194517
Patent Literature 6: Japanese Patent Application Publication No. 3280677
Patent Literature 7: Japanese Patent Application Publication No. 3304560

SUMMARY OF THE INVENTION

Problems to be Solved by the Invention

To ensure transmission/reception of harmonics of higher frequency, the electrode formed on the piezoelectric element must be made as thin as possible. This has made it difficult to ensure higher reliability in the connection of the piezoelectric element, electrode and wiring member in a limited space.

The space for connection with the lead wire is limited in the array type ultrasonic probe using the harmonic imaging technique. Thus, connection by lead wires as disclosed in Patent Literatures 4 and 5 will result in a poor yield rate and cannot be utilized.

Further, when the flexible printed substrate and electrode are laminated and bonded as shown in Patent Literature 6, the flexible printed substrate has a greater thickness. This will deteriorate the acoustic property of the piezoelectric element. Accordingly, this method is not suited for transmission and reception of higher harmonic ultrasonic waves.

According to the method illustrated in Patent Literature 7, if an electrode made up of a very thin metallic film is used to minimize an impact on the acoustic property of the piezoelectric element, the projecting portion of the electrode may be cracked by vibration. Especially when the projecting portion of the electrode is bent for installation, cracks are more likely to occur.

In view of the problems described above, it is an object of the present invention is to provide an ultrasonic probe capable of highly reliable connection between the electrode of a piezoelectric element and a wiring member, and an ultrasonic diagnostic device equipped with this highly reliable ultrasonic probe.

Means for Solving the Problems

To solve the aforementioned problem, the present invention has the following characteristics:

1. An ultrasonic probe including at least one transmission element layer for transmitting ultrasonic waves; at least one reception element layer receiving ultrasonic waves and providing an electrode on each of both surfaces opposed in a direction of a thickness; and at least one matching layer for matching acoustic impedance; and these layers being arranged in this order toward a direction of transmitting the ultrasonic waves, and wherein the reception element layer is provided with a projecting portion projecting in a direction of elevation from upper and lower layers which sandwich two electrodes respectively formed on both surfaces of the reception element layer, and at least one of the electrodes is formed by extending to the projecting portion.

2. The ultrasonic probe described in the Structure 1 wherein the reception element layer is formed of an organic resin and the projecting portion together with the electrodes are bent toward the transmission element layer.

3. The ultrasonic probe described in the Structure 1 or 2 wherein a thickness of the electrode formed on at least one of the surfaces of the projecting portion is greater than a thickness of the electrode formed other than on the projecting portion.

4. The ultrasonic probe described in any one of the Structures 1 to 3 wherein at least one of the electrodes formed on the projecting portion is covered with a protective layer.

5. The ultrasonic probe described in any one of the aforementioned Structures 1 to 4 wherein the electrodes are formed on both surfaces opposed in a direction of a thickness of the projecting portion, and are connected to conductive sections formed on both surfaces opposed in a direction of a thickness of a flexible substrate.

6. An ultrasonic diagnostic device provided with the ultrasonic probe described in any one of the Structures 1 to 5.

Effects of the Invention

According to the present invention, the reception element layer is provided with projecting portions projecting in the direction of elevation from the upper and lower layers which sandwich the reception element layer on both surfaces of which electrodes are formed, and at least one of the electrodes is formed by extending to the projecting portions. This structure provides an ultrasonic probe capable of highly reliable connection between the electrode of a piezoelectric element and a wiring member, and an ultrasonic diagnostic device equipped with this highly reliable ultrasonic probe.

DETAILED DESCRIPTION OF THE PREFERRED EMBODIMENTS

Figure 1:
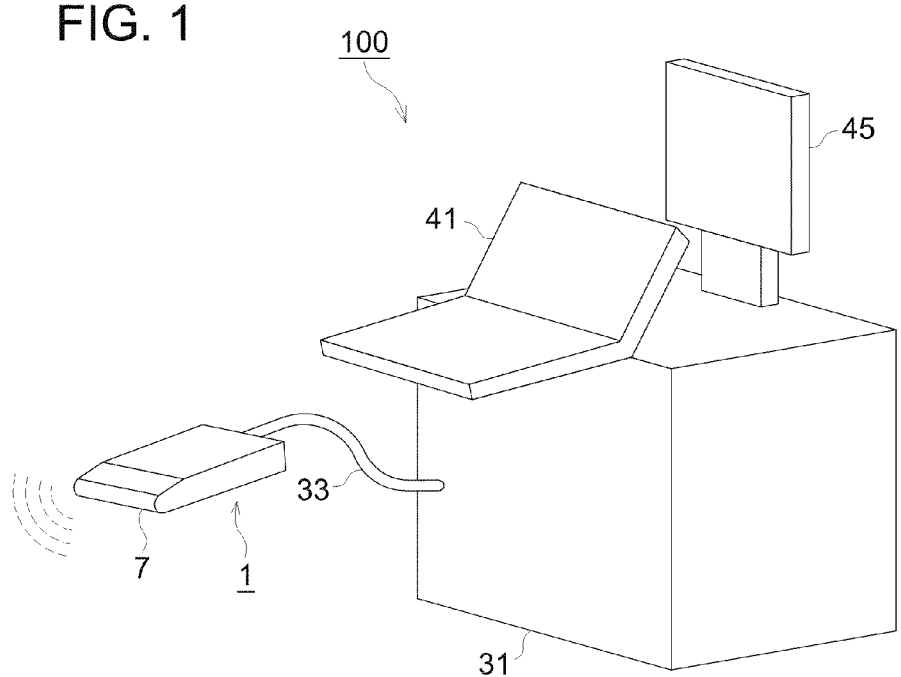
FIG. 1 is a drawing illustrating the external structure of the ultrasonic diagnostic device 100 in an embodiment.

The following describes an embodiment of the present invention with reference to drawings, without the present invention being restricted thereto. The same portions in the drawing assigned with the same numerals of reference will not be described to avoid duplication.

(Structures and Operations of the Ultrasonic Diagnostic Device and Ultrasonic Probe)

Figure 2:
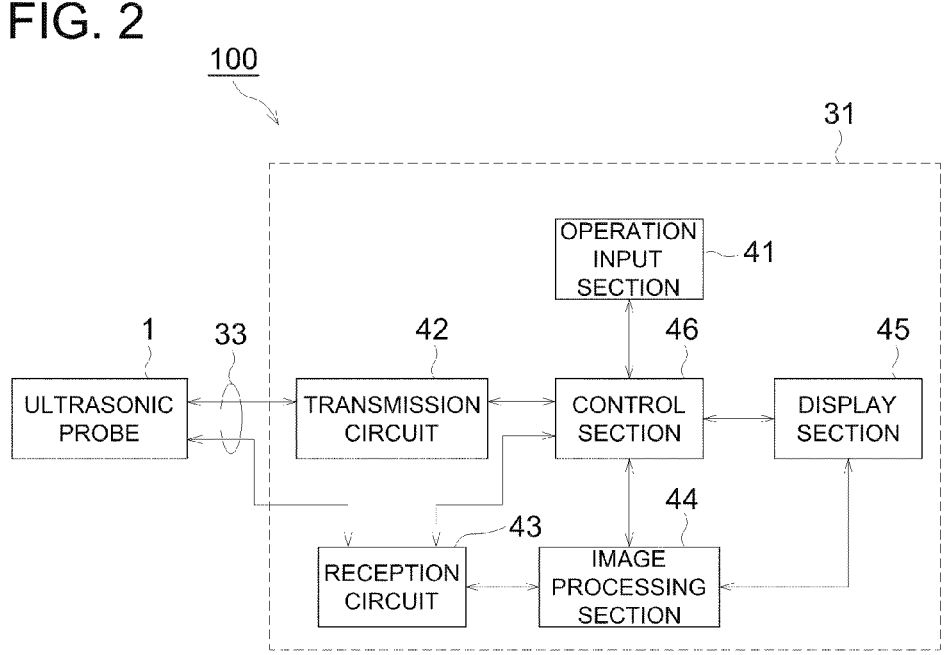
FIG. 2 is a block diagram showing the electric structure of the ultrasonic diagnostic device 100 in an embodiment.

FIG. 1 is a drawing representing the external structure of the ultrasonic diagnostic device in an embodiment. FIG. 2 is a block diagram showing the electric structure of the ultrasonic diagnostic device in an embodiment.

The ultrasonic diagnostic device 100 sends ultrasonic waves (ultrasonic signals) to the test subject such as a living body (not illustrated). From the reflection (echo, ultrasonic signal) of the ultrasonic waves reflected from the test subject having received the ultrasonic waves, the ultrasonic diagnostic device 100 forms an ultrasonic image of the internal conditions within the test subject, and displays this image on a display section 45.

The ultrasonic probe 1 sends ultrasonic waves (ultrasonic signals) to the test subject, and receives the ultrasonic waves reflected from the test subject. As shown in FIG. 2, the ultrasonic probe 1 is connected with an ultrasonic diagnostic device main body 31 through a cable 33, and is electrically connected with the transmission circuit 42 and reception circuit 43.

In response to the instruction from the control section 46, the transmission circuit 42 sends electric signals to the ultrasonic probe 1 through the cable 33, and ensures that ultrasonic waves are sent from the ultrasonic probe 1 to the test subject.

In response to the instruction from the control section 46, the reception circuit 43 receives from the ultrasonic probe 1 through the cable 33 the electric signal in conformance to the reflection of the ultrasonic waves coming from inside the test subject.

In response to the instruction from the control section 46, based on the electric signal received by the reception circuit 43, the image processing section 44 forms an image of the internal conditions of the test subject as an ultrasonic image.

The display section 45 is made up of a liquid crystal display panel and others. In response to the instruction from the control section 46, the display section 45 displays the ultrasonic image formed by the image processing section 44.

The operation input section 41 consists of a switch, key substrate and others, and is provided to allow a user to input the command for specifying the start of diagnosis or the data including the individual information on a test subject.

The control section 46 is made up of a CPU, memory and others. According to the procedure programmed on the basis of the input on the operation input section 41, the control section 46 controls various parts of the ultrasonic diagnostic device 100.

Figure 3:
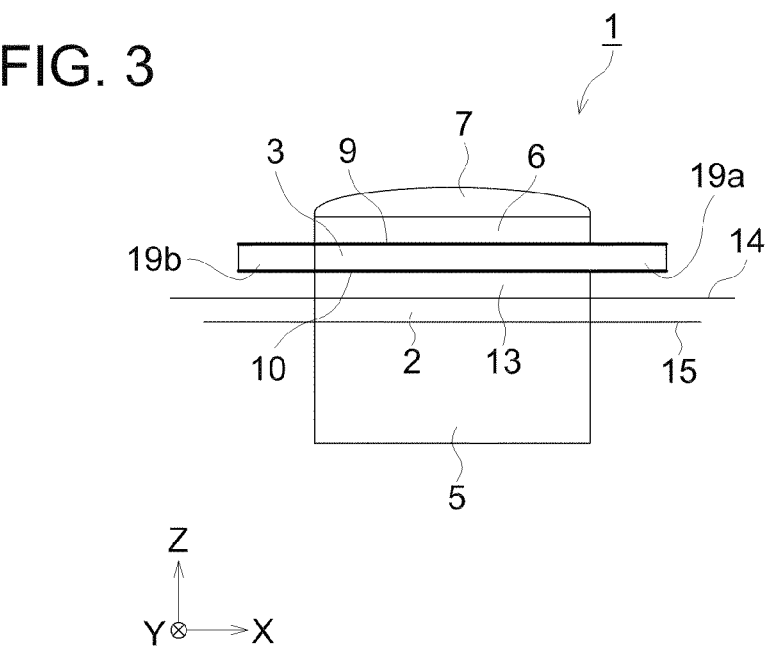
FIG. 3 is a cross sectional view representing the structure of the head section of the ultrasonic probe in the first embodiment.
Figure 4:
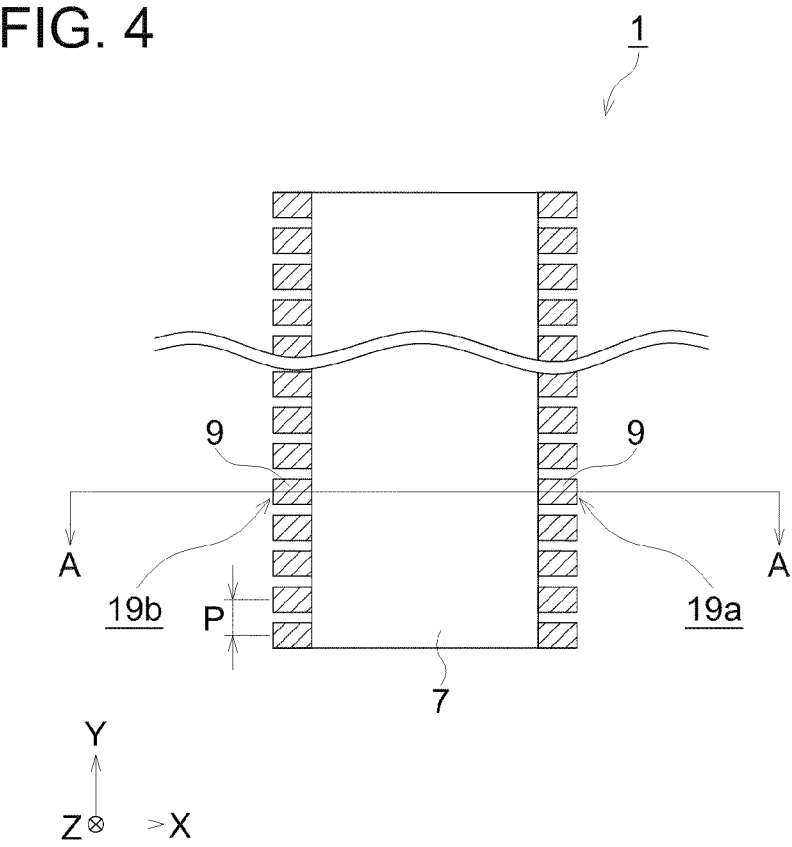
FIG. 4 is a plan view showing the reception element layer 3 of the ultrasonic probe of FIG. 3, as viewed from the positive Z-axis direction.

FIG. 3 is a cross sectional view representing the structure of the head section of the ultrasonic probe in the first embodiment. FIG. 4 is a plan view showing the reception element layer 3 of the ultrasonic probe of the first embodiment.

The following description is given with reference to the coordinates of X, Y and Z in the drawing. The X-axis direction indicates the direction of elevation (for dicing), and the positive Z-axis direction denotes the direction in which ultrasonic waves are emitted. The Z-axis direction represents the direction of lamination. FIG. 4 is a plan view showing the ultrasonic probe 1, as viewed from the direction in which ultrasonic waves are emitted (positive Z-axis direction). FIG. 3 is a cross sectional view showing a cross section taken along arrow line A-A in FIG. 4.

In the ultrasonic probe 1 of the first embodiment, a fourth electrode 15, transmission element layer 2, third electrode 14, intermediate layer 13, second electrode 10, reception element layer 3, first electrode 9, matching layer 6 and acoustic lens 7 are laminated in that order on the backing material 5, as shown in FIG. 3. The following description of various parts will be given in the order of laminates.

The transmission element layer 2 is a piezoelectric element composed of an inorganic material such as PZT (lead zirconate titanate). A third electrode 14 and fourth electrode 15 are mounted on both surfaces opposed direction of a thickness. The transmission element layer 2 is approximately 320 µm thick.

The third electrode 14 and fourth electrode 15 are connected to the cable 33 by means of a connector (not illustrated), and are further linked to the transmission circuit 42 through the cable 33. It is also possible to make such arrangements that, if electric signals are inputted into the third electrode 14 and fourth electrode 15, ultrasonic waves are sent in the Z-axis positive direction from the transmission element layer 2.

The third electrode 14 and fourth electrode 15 are approximately 1 to 2 µm thick. The thickness of the third electrode 14 and fourth electrode 15 is preferably minimized from the viewpoint of acoustics. If the thickness is excessively reduced, however, cracks will occur to the electrode and reliability will be lost. This thickness is preferably kept in the range of 0.1 to 10 µm, preferably in the range of 0.1 to 5 µm. Especially the thickness of the fourth electrode 15 from which ultrasonic waves are sent is preferably minimized for the purpose of maintaining good acoustic properties.

In the third electrode 14 and fourth electrode 15, such a metallic material as gold, silver and aluminum is used to form a film on both surfaces of the transmission element layer 2 by means of vapor deposition method or photolithography.

The intermediate layer 13 is made of a resin material. The intermediate layer 13 connects the second electrode 10 and third electrode 14, and absorbs the oscillation of the reception element layer 3 to ensure that the transmission element layer 2 will not be oscillated by resonance when the reception element layer 3 has received the ultrasonic waves reflected by the test subject.

The resin material used for the intermediate layer 13 is exemplified by polyvinyl butyral, polyolefin, polyacrylate, polyimide, polyamide, polyester, polysulfone, epoxy, and oxetane. Further, these resins can be mixed with fine particulates for adjustment of the properties thereof.

The thickness of the intermediate layer 13 is selected in conformance to the desired sensitivity and frequency characteristics. For example, the thickness is approximately in the range of 180 to 190 µm. Depending on the desired sensitivity and frequency characteristics, the intermediate layer 13 can be omitted.

The reception element layer 3 is composed of a plurality of piezoelectric elements that contain organic piezoelectric materials.

The organic piezoelectric material used to form the reception element layer 3 is exemplified by vinylidene fluoride polymer. Other examples of the organic piezoelectric material include the copolymer based on vinylidene fluoride (VDF). This vinylidene fluoride copolymer is a copolymer between vinylidene fluoride and other monomers. Other monomers include ethylene trifluoride (TrFE), tetrafluoroethylene (TeFE), perfluoroalkylvinylether (PFA), perfluoroalkoxyethylene (PAE) and perfluorohexanone ethylene.

Generally, the piezoelectric element of the inorganic piezoelectric material is capable of receiving only the ultrasonic waves in the frequency band equivalent to about twice the frequency of the fundamental waves. By contrast, the piezoelectric element made of organic piezoelectric material is capable of receiving the ultrasonic waves in the frequency band equivalent to about four through five times the frequency of the fundamental waves, and is therefore suited for increasing the bandwidth of the received frequency. The ultrasonic waves are received by an organic piezoelectric element 21 capable of receiving the ultrasonic waves over a wide frequency range, and therefore, the ultrasonic probe 1 and ultrasonic diagnostic device 100 having a simple structure in the present invention provide an increased frequency bandwidth.

The thickness of the reception element layer 3 can be set as appropriate, in conformance to the frequency of the ultrasonic waves to be received, or the type of the organic piezoelectric material. For example, when the ultrasonic waves having a center frequency of 15 MHz are to be received, the thickness of the reception element layer 3 is approximately in the range of 35 to 40 µm.

The first electrode 9 and second electrode 10 are formed on both surfaces opposed to each other direction of a thickness of the reception element layer 3 (in the Z-axis direction), respectively.

The thickness of the first electrode 9 and second electrode 10 are approximately in the range of 1 to 2 µm. The electrode of the reception element layer 3 is preferably minimized from the viewpoint of acoustics. If the thickness is excessively reduced, however, cracks will occur to the electrode and reliability will be lost. This thickness is preferably kept in the range of 0.1 to 10 µm, preferably in the range of 0.1 to 5 µm.

The reception element layer 3 receives the ultrasonic waves of high frequency. Accordingly, both the first electrode 9 and second electrode 10 are preferably minimized from the viewpoint of acoustics.

Such a metallic material as gold, silver and aluminum is used to form a film on the first electrode 9 and second electrode 10 by means of the vapor deposition method or photolithography. The electrode to be used for the reception element layer 3, especially the first electrode 9, must be formed in a very thin configuration to ensure reception of ultrasonic waves with high sensitivity. Thus, highly conductive gold is preferably used as a metallic material.

As illustrated in FIG. 3, the reception element layer 3 is provide with the projecting portions 19a and 19b projecting in the direction of elevation from the matching layer 6 as an upper layer sandwiching the first electrode 9 and second electrode 10 formed on both surfaces of the reception element layer 3, and the intermediate layer 13 as a lower layer. The first electrode 9 and second electrode 10 are each extended and formed on both the mutually opposed sides of the projecting portions 19a and 19b.

The reception element layer 3 of the aforementioned structure is flow-cast from the solution of the organic piezoelectric element to form a film having a prescribed thickness. After having been crystallized by heating, the film is formed into a sheet having prescribed dimensions, longer in the direction of elevation, from the upper and lower layers. The first electrode 9 and second electrode 10 are formed on both sides of the reception element layer 3 having been produced. Then the films of the first electrode 9 and second electrode 10 are formed on both the mutually opposed sides of the projecting portions 19a and 19b as well.

The present embodiment is described with reference to the case where the first electrode 9 and second electrode 10 are extended and formed on both the mutually opposed sides of the projecting portions 19a and 19b. However, it is only required that at least one of the first electrode 9 and second electrode 10 should be formed by extending to the projecting portions 19a and 19b. For example, one of the electrodes can extend toward the side opposite the projecting portion 19, without being formed on the projecting portion 19. Further, the projecting portions 19a and 19b are provided on both sides of the reception element layer 3 in the direction of elevation, but the projecting portion 19 can be provided on one of both sides.

The first electrode 9 and second electrode 10 are connected with the reception circuit 43 through the cable 33.

When the reception element layer 3 has received the ultrasonic waves reflected by the test subject, and is oscillated, an electric signal occurs to the piezoelectric element between the first electrode 9 and second electrode 10 in conformance to the reflected waves. The electric signal having occurred between the first electrode 9 and second electrode 10 is received by the reception circuit 43 through the cable 33 and is formed into an image by the image processing section 44.

The matching layer 6 has an intermediate impedance of the acoustic impedances of various layers, and provides matching of acoustic impedances. The present embodiment illustrates an example wherein the matching layer 6 is a single layer. This is also applicable to the case of multiple layers. In a single layer, the thickness of the matching layer 6 is approximately 140 µm, for example.

The acoustic lens 7 is made of a silicone and resin, and is used to converge the transmitted or received ultrasonic waves within a prescribed distance.

A transmission element layer 2 wherein the third electrode 14 and fourth electrode 15 are formed, an intermediate layer 13, a reception element layer 3 wherein the first electrode 9 and second electrode 10 are formed, and a matching layer 6 are adhered onto the packing material 5 in that order by an adherent, as shown in FIG. 3. After lamination, dicing is performed in the X-axis direction from the matching lager 18 toward the direction (in the negative Z-axis direction) opposite the traveling direction of the ultrasonic waves. Then dicing is further performed up to a depth of 100 µm in the negative Z-axis direction from the bonded layer of the backing material and fourth electrode. After the groove formed by dicing has been filled with a filler made of silicone resin or the like, an acoustic lens 7 is bonded on the topmost layer.

In the ultrasonic probe 1 produced in the aforementioned procedure, the projecting portions 19a and 19b having the first electrode 9 formed thereon project from the acoustic lens 7 as the upper layer or the matching layer 6 (not illustrated) toward both sides in the direction of elevation, as shown in FIG. 4. "P" of FIG. 4 denotes the interval between the diced projecting portions 19a and 19b in the Y-axis direction. FIG. 4 does not illustrate the third electrode 14 or fourth electrode 15 for ease of explanation.

Figure 5:
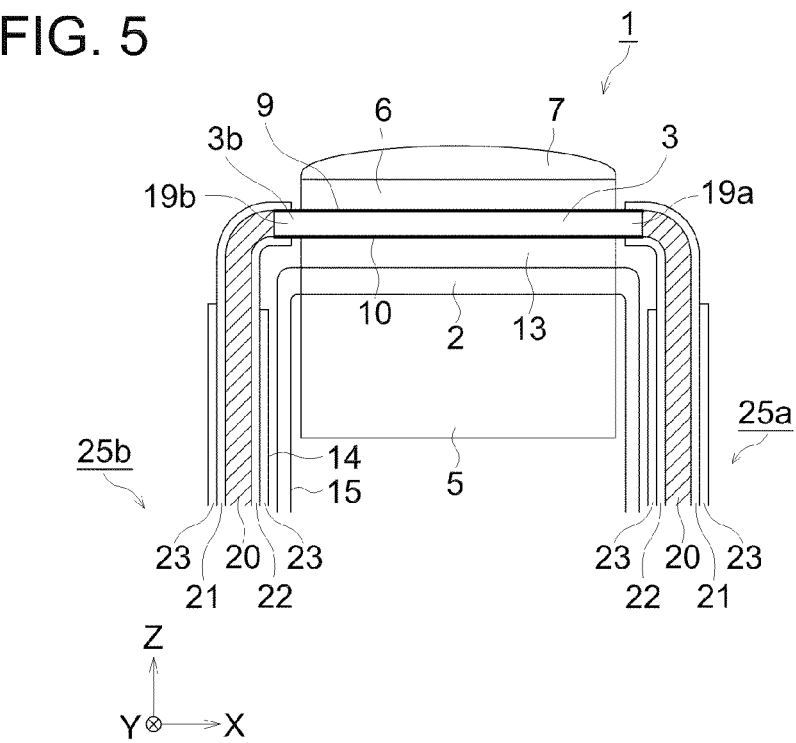
FIG. 5 is a cross sectional view illustrating the connection between the reception element layer 3 and flexible substrate in a first embodiment.

Referring to FIG. 5, the following describes the case where the first electrode 9 and second electrode 10 formed on both surfaces of the projecting portions 19a and 19b are connected with the flexible substrate 25.

FIG. 5 is a cross sectional view showing the connection between the reception element layer 3 and flexible substrate 25 in the first embodiment.

The flexible substrate 25 is a double faced substrate wherein the wiring pattern of copper foils 21 and 22 as conducting sections are formed on both surfaces of the substrate material 20.

The first electrode 9 formed on the projecting portion 19a and copper foil 21, and the second electrode 10 formed on the projecting portion 19b and copper foil 22 are respectively connected by the conductive adherent or soldering (not illustrated). The flexible substrates 25a and 25b are bent toward the transmission element layer 2 (in the negative Z-axis direction). The thickness of the copper foils 21 and 22 lies in the range of 3 through 50 µm. No problem occurs if these foils are bent.

The interval P of the diced projecting portions 19a and 19b of FIG. 4 in the Y-axis direction is extremely small. Mounting difficulties may arise if the wiring pattern of the portions of the flexible substrates 25a and 25b connected with the first electrode 9 and second electrode 10 is designed to have an equally spaced interval. In the present embodiment, the pattern of the portions of the flexible substrates 25a and 25b (not illustrated) connected with the first electrode 9 and second electrode 10 is designed to have a double space 2P so that the flexible substrates 25a and 25b will be connected alternately with the electrodes provided on the projecting portions 19a and 19b.

The copper foils 21 and 22 of the flexible substrates 25a and 25b covered with cover lays 23 are wired to prescribed positions, and are connected removably with the cable 33 by means of connectors (not illustrated) provided on the flexible substrates 25a and 25b.

As described above, in the present embodiment, the first electrode 9 and second electrode 10 are formed on the surfaces of the projecting portions 19a and 19b. This structure ensures easy connection with the flexible substrates 25a and 25b, and prevents the first electrode 9 or second electrode 10 from being cracked by vibration subsequent to connection. This structure enhances the reliability of the ultrasonic diagnostic device 100.

In addition to the double faced flexile substrate, a single faced flexible substrate and other wiring materials can be used for connection between the first electrode 9 and second electrode 10. Further, any one of the first electrode 9 and second electrode 10 can be formed on the surfaces of the projecting portions 19a and 19b.

Figure 6:
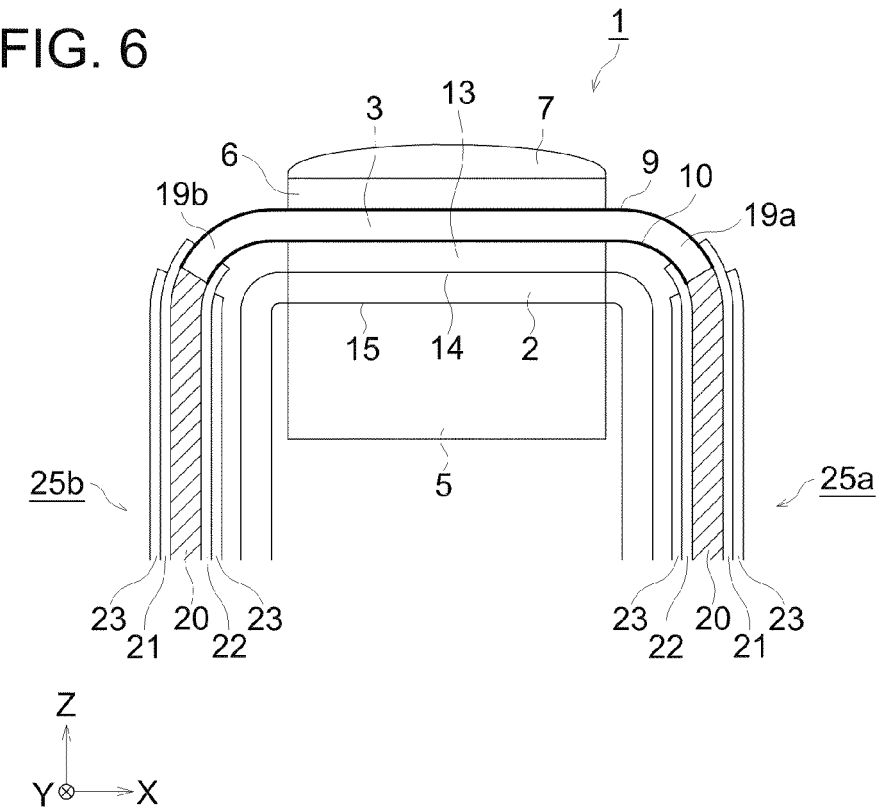
FIG. 6 is a cross sectional view illustrating the connection between the reception element layer 3 and flexible substrate in a second embodiment.

The following describes the second embodiment illustrated in FIG. 6. FIG. 6 is a cross sectional view illustrating the connection between the reception element layer 3 and flexible substrate 25 in the second embodiment. In the following description, the same functional components will be assigned with the same reference numerals, and description will be omitted to avoid duplication.

The difference between the second and first embodiment is found in that the projecting portions 19a and 19b are each bent toward the transmission element layer 2 (in the negative Z-axis direction) in the second embodiment. The reception element layer 3 can be easily bent because it is made of an organic piezoelectric element, as described above.

The first electrode 9 and second electrode 10 are each formed on the projecting portions 19a and 19b, and are respectively connected with the copper foils 21 and 22 by the conductive adhesive or soldering (not illustrated), as in the first embodiment. The first electrode 9 and copper foil 21, and second electrode 10 and copper foil 22 are respectively connected with each other by the conductive adhesive or soldering (not illustrated), and are bent toward the transmission element layer 2 (in the negative Z-axis direction).

As described above, the reception element layer 3 is made of an organic piezoelectric element in the present embodiment. This structure ensures that the projecting portions 19a and 19b projecting from the upper and lower layers of the reception element layer 3 are bent toward the transmission element layer 2, and are connected to the flexible substrates 25, whereby the width in the direction of elevation can be reduced for mounting. The first electrode 9 and second electrode 10 are formed on the surfaces of the projecting portions 19a and 19b. This arrangement permits easy connection with the flexible substrate 25, and eliminates the possibility of the electrode being cracked by vibration subsequent to connection. This structure enhances the reliability of the ultrasonic diagnostic device 100.

Figure 7:
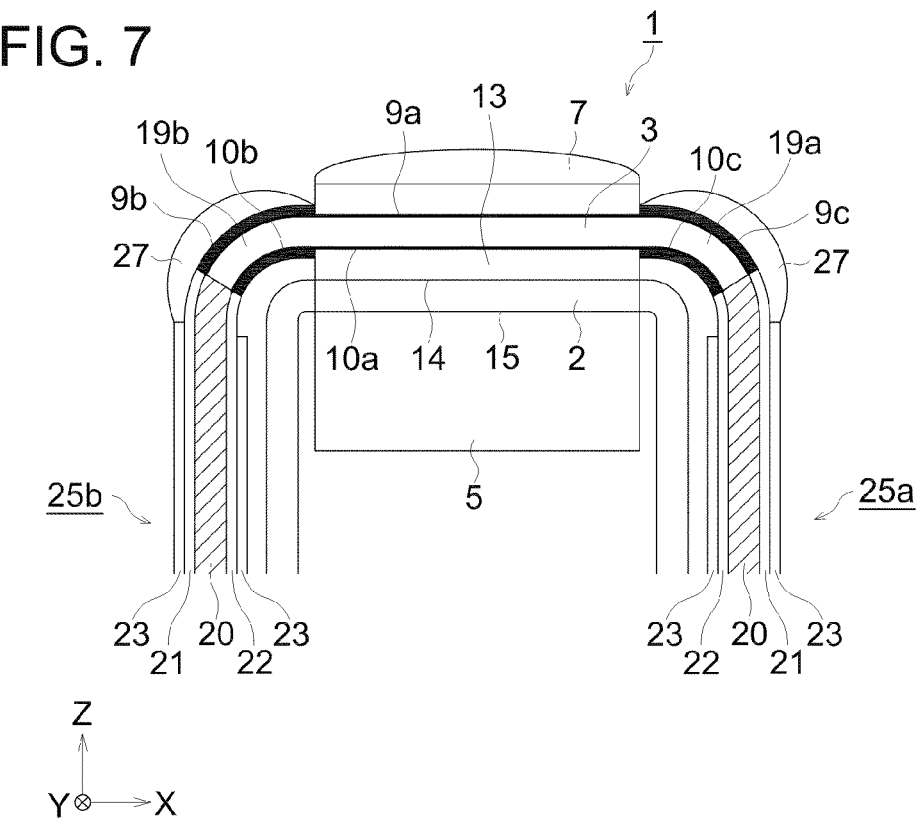
FIG. 7 is a cross sectional view illustrating the connection between the reception element layer 3 and flexible substrate in a third embodiment.

The following describes the third embodiment illustrated in FIG. 7. FIG. 7 is a cross sectional view showing the connection between the reception element layer 3 and flexible substrate 25.

The difference between the third and second embodiment is found in that the thicknesses of the first electrodes 9c and 9b and second electrodes 10c and 10b formed on the projecting portions 19a and 19b are respectively greater than those of the first electrode 9a and second electrode 10a of the laminated portion, and that the bent portion is covered with a protective layer 27.

After the first electrode 9a and second electrode 10a have been formed, the first electrodes 9c and 9b and second electrodes 10c and 10b are increased in thickness by masking the portions of the first electrodes 9c and 9b and second electrodes 10c and 10b, using the vapor deposition method or others. The protective layer 27 is cured by exposure to ultraviolet rays after the UV curable resin has been dropped onto the bent portion by the inkjet method or others.

As described above, an increase in the thickness of the electrodes formed on the projecting portions 19a and 19b allows the thickness of the electrodes of the laminated portion to be minimized, without reliability being lost. For example, even if the thickness of the first electrode 9a of the laminated portion is reduced to 0.5 μm, the thickness of the first electrodes 9c and 9b formed on the projecting portions 19a and 19b is kept within the range of 3 through 50 μm. Then, even if the thickness of the first electrodes 9c and 9b is reduced by several microns as a result of bending the projecting portions 19a and 19b, a sufficient thickness is still ensured, without any possibility of the electrode being cracked.

Further, when first electrode 9c and 9b is covered with the protective layer 27, reduced loads will be applied to the first electrodes 9c and 9b by vibration and others. This structure further enhances reliability.

Similarly, if the second electrodes 10c and 10b are reduced in thickness, the electrode may be separated or cracked by bending. However, if the thickness is kept in the range of about 3 through 50 μm, the loads applied to the bent portion are absorbed, with the result that the possibility of cracking is eliminated.

In the present embodiment, the thicknesses of the first electrodes 9c and 9b and second electrodes 10c and 10b are respectively greater than those of the first electrode 9a and second electrode 10a. However, any of the first electrodes 9c and 9b or second electrodes 10c and 10b can be increased in thickness. Further, the protective layers 27 can be provided on the sides of the second electrodes 10c and 10b.

Figure 8:
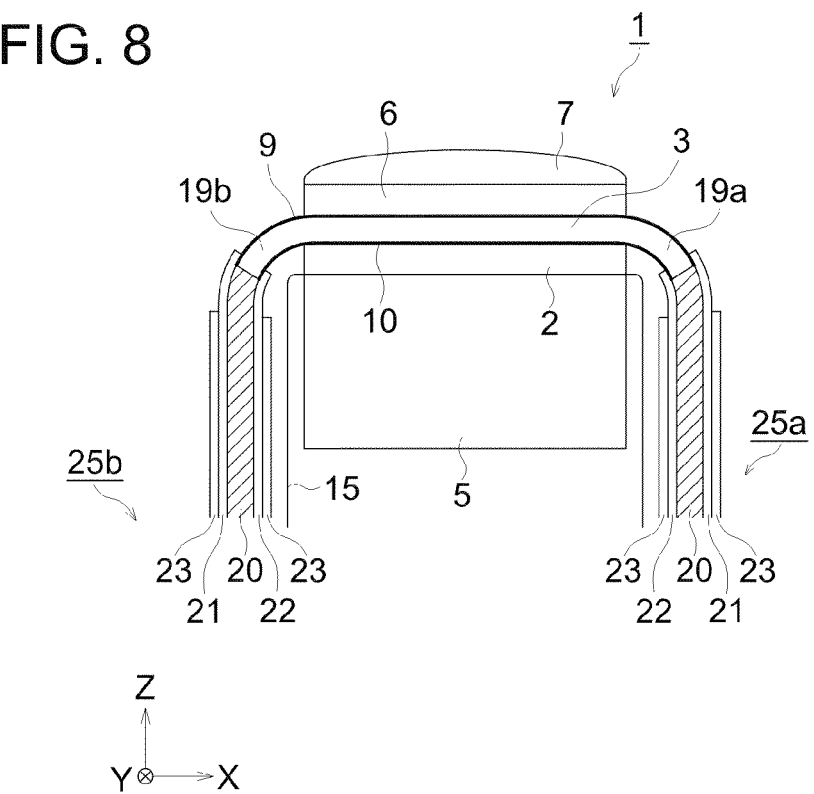
FIG. 8 is a cross sectional view illustrating the connection between the reception element layer 3 and flexible substrate in a fourth embodiment.

The following describes the fourth embodiment illustrated in FIG. 8. FIG. 8 is a cross sectional view showing the connection between reception element layer 3 and flexible substrate 25 in the fourth embodiment.

The fourth embodiment is an example wherein the present invention is applied to the ultrasonic probe 1 devoid of an intermediate layer 13.

In the ultrasonic probe 1 of FIG. 8, a fourth electrode 15, transmission element layer 2, second electrode 10, reception element layer 3, first electrode 9, matching layer 6 and acoustic lens 7 are laminated in that order on the backing material 5.

The third electrode 14 and intermediate layer 13 are omitted, and the second electrode 10 serves as a common electrode for the transmission element layer 2 and reception element layer 3. The present embodiment shows an example wherein the first electrode 9 and second electrode 10 formed on the bent projecting portions 19a and 19b are connected with the flexible substrates 25a and 25b, as in the second embodiment. However, the structures of the first embodiment and third embodiment can be used in this fourth embodiment.

As described above, the present invention provides an ultrasonic probe capable of ensuring highly reliable connection of the electrode of the piezoelectric element and wiring member, and an ultrasonic diagnostic device equipped with a highly reliable ultrasonic probe.

DESCRIPTION OF REFERENCE NUMERALS

1. Ultrasonic probe
2. Transmission element layer
3. Reception element layer
5. Backing material
6. Matching layer
9. First electrode
10. Second electrode
13. Intermediate layer
14. Third electrode
15. Fourth electrode
19. Projecting portion
20. Substrate material
21, 22. Copper foil
23. Cover lay
25. Flexible substrate
27. Protective layer
31. Ultrasonic diagnostic device main body 33. Cable
41. Operation input section
42. Transmission circuit
43. Reception circuit
44. Image processing section
45. Display section
46. Control section
100. Ultrasonic diagnostic device

What is claimed is:

1. An ultrasonic probe comprising:
   at least one transmission element layer for transmitting ultrasonic waves;
   at least one reception element layer for receiving ultrasonic waves, wherein an electrode is provided on each of both surfaces opposed in a direction of thickness of the reception element layer;
   a flexible substrate provided with conductive sections provided in two layers on opposite surfaces thereof that are opposed in a direction of thickness of the flexible substrate; and
   at least one matching layer for matching acoustic impedance;
   wherein the transmission element layer, the reception element layer, and the matching layer are arranged in this order in a direction of transmitting the ultrasonic waves;
   wherein the reception element layer is provided with a projecting portion projecting in a direction of elevation from upper and lower layers which sandwich the electrodes respectively formed on both surfaces of the reception element layer;
   wherein the electrodes provided on both of the surfaces of the reception element layer extend so as to be provided on both surfaces of the projecting portion which are opposed in a direction of thickness of the projecting portion, and the electrodes provided on both of the surfaces of the projecting portion are respectively connected to the two layers of the conductive sections provided on the opposite surfaces of the flexible substrate; and
   wherein the reception element layer is formed of an organic resin, and the projecting portion together with the electrodes are bent toward the transmission element layer.

2. The ultrasonic probe of claim 1, wherein a thickness of the electrode formed on at least one of the surfaces of the projecting portion is greater than a thickness of the electrode formed other than on the projecting portion.

3. The ultrasonic probe of claim 1, wherein at least one of the electrodes formed on the projecting portion is covered with a protective layer.

4. An ultrasonic diagnostic device provided with the ultrasonic probe of claim 1.

5. The ultrasonic probe of claim 1, wherein the reception element layer is provided with a plurality of the projecting portions, which are arranged at a predetermined interval along two edges thereof;
   wherein the ultrasonic probe comprises two of the flexible substrates provided respectively at the two edges of the reception element layer; and
   wherein the conductive sections of each of the two flexible substrates are spaced apart at twice the predetermined interval, and connections between the conductive sections of the two flexible substrates and the electrodes provided on the surfaces of the projecting portions are alternated between the two flexible substrates.

* * * * *